United States Patent [19]
Illig et al.

[11] Patent Number: 5,741,819
[45] Date of Patent: Apr. 21, 1998

[54] ARYLSULFONYLAMINOBENZENE DERIVATIVES AND THE USE THEREOF AS FACTOR XA INHIBITORS

[75] Inventors: Carl R. Illig, Phoenixville, Pa.; Richard M. Soll, Lawrenceville, N.J.; Joseph M. Salvino, Schwenksville, Pa.; Bruce E. Tomczuk, Collegeville, Pa.; Tianbao Lu, Exton, Pa.; Nalin L. Subasinghe, West Chester, Pa.

[73] Assignee: 3-Dimensional Pharmaceuticals, Inc., Exton, Pa.

[21] Appl. No.: 488,196

[22] Filed: Jun. 7, 1995

[51] Int. Cl.$^6$ .......................... A61K 31/18; A61K 31/24; A61K 31/44

[52] U.S. Cl. .......................... 514/602; 514/305; 514/357; 514/535; 514/603; 514/604; 564/84; 564/86; 564/90; 564/91; 560/10; 560/13; 562/429; 562/430; 546/133; 546/334

[58] Field of Search .................. 546/334, 133; 514/357, 305, 535, 602, 603, 604; 560/10, 13; 564/84, 86, 90, 91; 562/429, 430

[56] References Cited

U.S. PATENT DOCUMENTS 5,385,885   1/1995   Gasic et al. .................. 514/12

FOREIGN PATENT DOCUMENTS

| WO 93/15756 | 8/1993 | WIPO . |
| WO 94/13693 | 6/1994 | WIPO . |
| WO 94/17817 | 8/1994 | WIPO . |
| WO 94/20468 | 9/1994 | WIPO . |
| WO 94/20526 | 9/1994 | WIPO . |
| WO 94/20535 | 9/1994 | WIPO . |

OTHER PUBLICATIONS

El-Sharief, A.M. et al., "2,5-Dichlorobenzenesulfonamide Derivatives and Their Biological Activities," *Indian Journal of Chemistry*, 22B: 700–704 (Jul. 1983).

Brana et al., Industrial production of N-(4-pyridylmethyl)benzamide, *Chemical Abstracts* 96:181160 (1981).

Church and Hoffman, Heparin Cofactor II and Thrombin: Heparin–Binding Proteins Linking Hemostasis and Inflammation, *Trends in Cardiovascular Medicine* 4(3):140–146 (1993).

Claeson G., Synthetic peptides and peptidomimetics as substrates and inhibitors of thrombin and other proteases in the blood coagulation system, *Blood Coagulation and Fibrinolysis* 5:411–436 (Jun. 1994).

Coughlin S.R., Molecular Mechanisms of Thrombin Signaling, *Seminars in Hematology* 31(4):270–277 (Oct. 1994).

Hara et al., DX-9065a, a New Synthetic, Potent Anticoagulant and Selective Inhibitor for Factor Xa, *Thrombosis and Hemostasis* 71:314–319 (Mar. 1994).

Harker L.A., Strategies for inhibiting the effects of thrombin, *Blood Coagulation and Fibrinolysis* 5 (*Suppl 1*):S47–S58 (Jan. 1994).

Hidaka et al., Preparation of sulfonylaminobenzylamine derivatives and heterocycle-containing benzylamine derivatives as ulcer inhibitors, *Chemical Abstracts* 122:9661 (Mar. 1994).

Lefkovits and Topol, Direct Thrombin Inhibitors in Cardiovascular Medicine, *Circulation* 90(3):1522–1536 (Sep. 1994).

Markwardt F., Inventory of Coagulation Inhibitors from Animals Feeding on Blood, *Thrombosis and Hemostasis* 72(3):477–479 (Sep. 1994).

Mellott et al., Acceleration of Recombinant Tissue–Type Plasminogen Activator–Induced Reperfusion and Prevention of Reocclusion by Recombinant Antistasin, a Selective Factor Xa Inhibitor, in a Canine Model of Femoral Arterial Thrombosis, *Circulation Research* 70:1152–1160 (1992).

Nagahara et al., Dibasic (Amidinoaryl)propanoic Acid Derivatives as Novel Blood Coagulation Factor Xa Inhibitors, *Journal of Medicinal Chemistry* 37:1200–1207 (Apr. 1994).

Ragosta et al., Specific Factor Xa Inhibition Reduces Restenosis After Balloon Angioplasty of Atherosclerotic Femoral Arteries in Rabbits, *Circulation* 89:1262–1271 (Mar. 1994).

(List continued on next page.)

*Primary Examiner*—Amelia Owens
*Attorney, Agent, or Firm*—Sterne, Kessler, Goldstein & Fox, P.L.L.C.

[57] ABSTRACT

The present invention is directed to non-peptidic factor Xa inhibitors which are useful for the treatment of arterial and venous thrombotic occlusive disorders, inflammation, cancer, and neurodegenerative diseases. The factor Xa inhibitors provide compounds of structure:

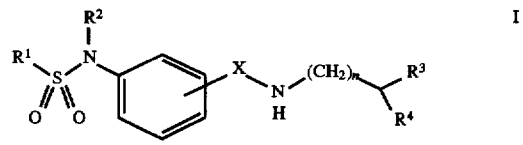

or pharmaceutically acceptable salts thereof;

wherein
$R^1$ is alkyl, substituted alkyl, cycloalkyl, aryl, substituted aryl, heteroaryl or substituted heteroaryl; $R^2$ is one of hydrogen, alkyl, cycloalkyl or aryl; $R^3$ is one of hydrogen, hydroxy or alkoxy; $R^4$ is one of $-NH_2$, phenyl or pyridyl, wherein said phenyl and said pyridyl are optionally substituted with one or two of halogen, hydroxy, hydroxyalkyl, alkoxy, amino, monoalkylamino, dialkylamino, aminoalkyl, monoalkylaminoalkyl and/or dialkylaminoalkyl; X is one of $-CH_2-$ or $-C(O)-$; and n is from zero to eleven; provided that when $R^4$ is $-NH_2$, then $R^3$ is hydrogen and n is other than zero; and also provided that when $R^3$ is hydroxy or alkoxy, then $R^4$ is other than $-NH_2$, and n is other than zero.

27 Claims, No Drawings

OTHER PUBLICATIONS

Raj et al., Long-term Oral Anticoagulant Therapy: Update on Indicators, Therapeutic Ranges, and Monitoring, *The American Journal of the Medical Sciences* 307(2):128–32 (Feb. 1994).

Seymour et al., Ecotin Is a Potent Anticoagulant and Reversible Tight-Binding Inhibitor of Factor Xa, *Biochemistry* 33:3949–3959 (Apr. 1994).

Sitko et al., Conjunctive Enhancement of Enzymatic Thrombolysis and Prevention of Thrombotic Reocclusion With the Selective Factor Xa Inhibitor, Tick Anticoagulant Peptide, *Circulation* 85:805–815 (1992).

Stürzebecher et al., Synthetic Inhibitors of Bovine Factor Xa and Thrombin Comparison of Their Anticoagulant Efficiency, *Thrombosis Research* 54:245–252 (1989).

Tapparelli et al., Synthetic low–molecular weight thrombin inhibitors: molecular design and pharmacological profile, *Trends in Pharmacological Sciences* 14:366–376 (1993).

Tidwell et al., Strategies for Anticoagulation with Synthetic Protease Inhibitors, Xa Inhibitors versus Thrombin Inhibitors, *Thrombosis Research* 19:339–349 (1980).

Weitz and Hirsh, New Anticoagulant Strategies, *Journal of Laboratory Clinical Medicine* 122(4):364–373 (1993).

Yamazaki et al.,Effects of DX–9065a, on Orally Active, Newly Synthesized and Specific Inhibitor of Factor Xa, against Experimental Disseminated Intravascular Coagulation in Rats, *Thrombosis and Hemostasis* 72(3):393–396 (Sep. 1994).

ARYLSULFONYLAMINOBENZENE DERIVATIVES AND THE USE THEREOF AS FACTOR XA INHIBITORS

FIELD OF THE INVENTION

The present invention relates to compounds that are inhibitors of thrombin production via factor Xa inhibition, their pharmaceutically acceptable salts, and pharmaceutically acceptable compositions thereof. The compounds and compositions are useful in the treatment of arterial and venous thrombotic occlusive disorders, inflammation and cancer.

BACKGROUND OF THE INVENTION

The serine protease thrombin occupies a central role in hemostasis and thrombosis (Tapparelli et al., *Trends in Pharmacological Sciences* 14:366–376 (1993); Lefkovits and Topol, *Circulation* 90(3):1522–1536 (1994); Harker, *Blood Coagulation and Fibrinolysis* 5 (Suppl 1):S47–S58 (1994)). Activation of the coagulation cascade through either the intrinsic pathway (contact activation) or the extrinsic pathway (activation by exposure of plasma to a non-endothelial surface, damage to vessel walls, or tissue factor release) leads to a series of biochemical events that converge on thrombin. Thrombin cleaves fibrinogen, ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism.

As a multifactorial protein, thrombin induces a number of effects on platelets, endothelial cells, smooth muscle cells, leukocytes, the heart, and neurons (Tapparelli et al., *Trends in Pharmacological Sciences* 14:366–376 (1993); Church and Hoffman, *Trends in Cardiovascular Medicine* 4(3):140–146 (1993)). Platelet activation leads to shape change and aggregation as well as the synthesis, release and secretion of vasoactive substances and lysosomal enzymes. Endothelial cell activation results in the secretion of stimulatory agents leading to increased vascular permeability and adhesiveness for mononuclear cells, one consequence of which is extravasation of leukocytes at the site of thrombin generation. Thrombin induces fibroblast and smooth muscle cell proliferation suggesting that thrombin plays a key role in lesion development following vascular damage. Enhanced automaticity and prolongation of repolarization have been observed in cardiac myocytes showing sensitivity to thrombin. Normal neuronal development has been shown also to be influenced by thrombin. Thus, inhibitors of thrombin function have therapeutic potential in a host of cardiovascular and non-cardiovascular diseases, including: myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoaguability during chemotherapy; Alzheimer's disease; and Down's syndrome.

To date only three classes of compounds (heparins, low-molecular weight heparins and coumarins, such as warfarin) have been used in anticoagulant therapy. Each class has severe limitations and liabilities (Weitz and Hirsh, *Journal of Laboratory Clinical Medicine* 122:364–373 (1993); Raj et al., *The American Journal of the Medical Sciences* 307 (2):128 (1994)). All three classes indirectly inhibit thrombin. Heparin and low-molecular weight heparins augment antithrombin III and/or heparin cofactor II inhibition of thrombin, whereas coumarins inhibit vitamin K-dependent post-translational modifications. Close monitoring and titration of therapeutic doses is required when employing these agents due to patient variability. Hemorrhagic complications due to bleeding are an encountered side effect. In fact, bleeding remains as the most common side effect of long term oral anticoagulant therapy. Lack of activity in arterial thrombosis in the case of heparin is due to its inability to inhibit clot bound thrombin. Lack of oral activity in the case of heparins and low-molecular weight heparins preclude their use for chronic administration.

Direct thrombin inhibitors of various structural classes have been identified recently (Tapparelli et al., *Trends in Pharmacological Sciences* 14:366–376 (1993); Claeson, *Blood Coagulation and Fibrinolysis* 5:411–436 (1994); Lefkovits and Topol, *Circulation* 90(3):1522–1536 (1994)). Representative compounds that act by inhibiting the active site of thrombin include the α-chloroketone D-phenylalanyl-L-prolyl-L-arginyl chloromethylketone (PPACK), the boro-arginine DUP714, the peptide arginal GYK114766, the cyclic peptides cyclotheonamides A and B, the benzamidine NAPAP, and the arylsulphonylarginine argatroban. The thrombin inhibitory peptides hirudin and hirulogs additionally span through the active and exosite domains of thrombin. The peptide hirugen and single-stranded DNA aptamers inhibit thrombin through exosite occupancy. These classes of antithrombotic agents still suffer from one or more of the following liabilities: (1) poor oral bioavailability due to the peptidic or oligonucleotidic nature of these agents, or high molecular weight or charged nature of the agents; (2) excessive bleeding complications; (3) poor selectivity towards thrombin versus other serine proteases (that may lead to severe and sometimes fatal hypotension and respiratory depression in animal models); (4) liver toxicity; or (5) cost effectiveness.

An alternative approach for inhibiting thrombin function is to inhibit factor Xa. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47–S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47–S58 (1994)). Indeed, continuous generation of new thrombin rather than reexposure of preformed clot-bound thrombin is thought to be responsible in part for the phenomenon of reocclusion since markers of thrombin generation have been found to increase during and after thrombolytic treatment for myocardial infarction. Thus, it is now believed that increased thrombin activity associated with thrombolysis is due at least in part to new thrombin generation.

Specific protein factor Xa inhibitors, such as the leech-derived, 119-amino acid protein antistasin and the soft tick-derived protein TAP (tick anticoagulant peptide) accelerated clot lysis and prevented reocclusion when given as adjuncts to thrombolysis (Mellott et al., *Circulation Research* 70:1152–1160 (1992); Sitko et al., *Circulation* 85:805–815 (1992)). U.S. Pat. No. 5,385,885, issued Jan. 31, 1995, discloses smooth muscle cell proliferation inhibitory activity of both TAP and antistasin. Additionally, TAP and antistasin have been shown to reduce experimental restenosis. These results suggest that factor Xa may play a role in the restenosis process through its effects upon thrombus formation or through its mitogenic potential (Ragosta et al., *Circulation* 89:1262–1271 (1994)). The peptide ecotin is another selective, reversible, tight-binding inhibitor of factor Xa that exhibits potent anticoagulant activity (Seymour et al., *Biochemistry* 33:3949–3959 (1994); PCT Published Application WO 94/20535, published Sep. 14, 1994). Ixodidae, argasin, and ancylostomatin are other representative peptidic factor Xa inhibitors isolated from animals that feed on blood (Markwardt, *Thrombosis and Hemostasis* 72:477–479 (1994)).

Non-peptide diamidino derivatives, such as (+)-(2S)-2-[4-[[(3S)-1-acetimidoyl-3-pyrrolidinyl]oxy]phenyl]-3-[7-amidino-2-naphthyl]propanoic acid hydrochloride pentahydrate (DX-9065a), exhibit anticoagulant activity (Tidwell et al., *Thrombosis Research* 19:339–349 (1980); Yamazaki et al., *Thrombosis and Hemostasis* 72:393–395 (1994); Hara et al., *Thrombosis and Hemostasis* 71:314–319 (1994); Nagahara et al., *Journal of Medicinal Chemistry* 37:1200–1207 (1994)). Synthetic amidino derivatives of phenylalanine and cycloheptanone have also shown potent factor Xa inhibition (Sturzebecher et al., *Thrombosis Research* 54:245–252 (1989)).

PCT Published Application WO 94/13693, published Jun. 23, 1994, discloses peptide analogs containing an aldehyde grouping. The application discloses that the analogs have substantial potency and specificity as inhibitors of mammalian factor Xa.

PCT Published Applications WO 93/15756, published Aug. 19, 1993, and WO 94/17817, published Aug. 18, 1994, disclose peptidyl arginine aldehydes that exhibit factor Xa and/or thrombin inhibitory activity.

PCT Published Application WO 94/20526, published Sep. 15, 1994, discloses peptide derivatives having a C-terminal boronic acid group. The application discloses that these peptide derivatives possess protein-inhibiting activity and are potent thrombin inhibitors.

PCT Published Application WO 94/20468, published Sep. 15, 1994, discloses 4-aminopyridine derivatives taught to be useful as antithrombotic agents.

Chemical Abstracts 96:181160 (1981) discloses N-(4-pyridylmethyl)benzamides and methods for the industrial production thereof. In particular, the compound 4-[(phenylsulfonyl)amino]-N-(4-pyridylmethyl)benzamide is disclosed.

Chemical Abstracts 122:9661 (1994) discloses sulfonylaminobenzylamine derivatives and the use thereof as ulcer inhibitors. In particular, the compound N-2-[[[(4-chlorophenyl) methyl]methylamino]methyl]phenyl-5-quinolinesulfonamide is disclosed.

SUMMARY OF THE INVENTION

The present invention is directed to novel arylsulfonylaminobenzamide or arylsulfonylaminobenzamine derivatives of Formula I (below). Also provided is a process for preparing compounds of Formula I. The novel compounds of the present invention exhibit antithrombotic activity via factor Xa inhibition. Also provided is a method of treating thrombosis, ischemia, stroke, restenosis, or inflammation in a mammal in need of such treatment, comprising administering to said mammal an effective amount of a compound of Formula I. Further provided is a pharmaceutical composition comprising a compound of Formula I and one or more pharmaceutically acceptable carriers or diluents.

DETAILED DESCRIPTION OF THE PREFERRED EMBODIMENTS

A first embodiment of the present invention is directed to a method of treating thrombosis, ischemia, stroke, restenosis or inflammation comprising administering to a mammal in need of said treatment a therapeutically or prophylactically effective amount of a compound of Formula I:

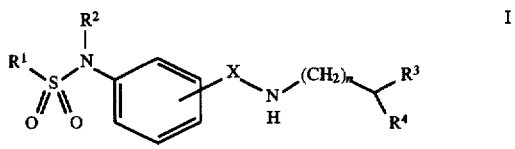

or pharmaceutically acceptable salts thereof;

wherein $R^1$ is alkyl, substituted alkyl, cycloalkyl, aryl, substituted aryl, heteroaryl or substituted heteroaryl;

$R^2$ is one of hydrogen, alkyl, cycloalkyl, aryl or aralkyl;

$R^3$ is one of hydrogen, hydroxy or alkoxy;

$R^4$ is one of —$NH_2$, phenyl, or $C_{3-10}$heterocycle having one or two nitrogen atoms, wherein said phenyl and said $C_{3-10}$heterocycle are optionally substituted with one or two of halogen, hydroxy, hydroxyalkyl, alkoxy, amino, monoalkylamino, dialkylamino, aminoalkyl, monoalkylaminoalkyl, and/or dialkylaminoalkyl;

X is one of —$CH_2$— or —C(O)—;

n is from zero to eleven; and wherein X is attached to the benzene ring in a position ortho-, meta- or para- to the sulfonylamino group;

provided that when $R^4$ is —$NH_2$, then $R^3$ is hydrogen and n is other than zero; and also provided that when $R^3$ is hydroxy or alkoxy, then $R^4$ is other than —$NH_2$, and n is other than zero.

A second aspect of the present invention is directed to novel compounds, and pharmaceutical compositions thereof, having the Formula I (above), or pharmaceutically acceptable salts thereof;

wherein $R^1$ is alkyl, substituted alkyl, cycloalkyl, aryl, substituted aryl, heteroaryl or substituted heteroaryl;

$R^2$ is one of hydrogen, alkyl, cycloalkyl, aryl or aralkyl;

$R^3$ is one of hydrogen, hydroxy or alkoxy;

$R^4$ is one of —$NH_2$, phenyl, or $C_{3-10}$heterocycle having one or two nitrogen atoms, wherein said phenyl and said $C_{3-10}$heterocycle are optionally substituted with one or two of halogen, hydroxy, hydroxyalkyl, alkoxy, amino, monoalkylamino, dialkylamino, aminoalkyl, monoalkylaminoalkyl, and/or dialkylaminoalkyl;

X is one of —$CH_2$— or —C(O)—; and n is from zero to eleven; and wherein X is attached to the benzene ring in a position ortho-, meta- or para- to the sulfonylamino group; provided that when $R^4$ is —$NH_2$, then $R^3$ is hydrogen and n is other than zero; and also provided that when $R^3$ is hydroxy or alkoxy, then $R^4$ is other than —$NH_2$, and n is other than zero; further provided that when $R^2$ is hydrogen or methyl, while $R^3$ is hydrogen, $R^4$ is pyridyl, X is —C(O)—, and n is zero or one, then $R^1$ is other than unsubstituted phenyl.

When $R^1$ is heteroaryl or substituted heteroaryl, preferred heteroaryl groups include pyridyl, thienyl, chromenyl, benzoxazolyl, quinazolinyl, quinolinyl and tetrahydroquinolinyl. Preferred groups when $R^1$ is substituted heteroaryl include those heteroaryl groups mentioned as preferred, having one or more substituents selected from halogen, $C_{1-6}$alkyl, $C_{1-6}$alkoxy, carboxy, amino, $C_{1-6}$alkylamino and/or di($C_{1-6}$)alkylamino.

When $R^4$ is $C_{3-8}$heterocycle, preferred values of $R^4$ include quinuclidinyl, piperidinyl, morpholinyl, pyrrolidinyl, pyridinyl, pyrimidinyl and imidazole.

Preferred values of $R^4$ include —$NH_2$, phenyl, 2-pyridyl, 4-pyridyl, 3-quinuclidyl, piperidinyl and aminomethylphenyl.

It is to be understood that Formula I allows the arylsulfonylamino moiety to be attached in any of the ortho-, meta- or para- positions, relative to group X, with meta- being preferred.

Preferred compounds of the present invention are those of Formula I wherein $R^1$ is optionally substituted $C_{6-12}$aryl, more preferably $C_{6-10}$aryl; $R^2$ is one of hydrogen, $C_{1-8}$alkyl, $C_{3-8}$cycloalkyl or $C_{6-12}$aryl; $R^3$ is one of hydrogen, hydroxy or $C_{1-8}$alkoxy; $R^4$ is one of —$NH_2$, phenyl or pyridyl, wherein said phenyl and pyridyl are optionally substituted with one or two of halogen, hydroxy, $C_{1-8}$alkoxy, amino, mono($C_{1-4}$)alkylamino, di($C_{1-4}$)alkylamino, or amino($C_{1-4}$)alkyl; X is —C(O)—; and n is zero to eight.

Most preferred are compounds of Formula I wherein $R^1$ is phenyl, aminophenyl or naphthyl; $R^2$ is hydrogen or $C_{1-4}$ alkyl; $R^3$ is hydrogen, hydroxy or $C_{1-4}$alkoxy; $R^4$ is one of —$NH_2$, phenyl, pyridyl, 3-hydroxyphenyl, 4-hydroxyphenyl, 4-hydroxy-3-methoxyphenyl, 3-hydroxy-4-methoxyphenyl, 4-dimethylaminophenyl and 3-aminomethylphenyl. When $R^4$ is —$NH_2$, most preferred values of n include 3, 4 and 7. When $R^4$ is optionally substituted phenyl or optionally substituted pyridyl, most preferred values of n include zero and one.

Thus, the following compounds are most preferred: 3-[(2-naphthalenylsulfonyl)amino]-N-[2-hydroxy-2-(3'-hydroxyphenyl)ethyl]benzamide; 3-[(2-naphthalenylsulfonyl)amino]-N-[2-hydroxy-2-(4'-hydroxyphenyl)ethyl]benzamide; 3-[(2-naphthalenylsulfonyl)amino]-N-[4'-[(N',N'-dimethylamino)-phenyl]methyl]benzamide; 3-[(phenylsulfonyl)amino]-N-[(4-hydroxy-3-methoxyphenyl)methyl]benzamide; 3-[(phenylsulfonyl)amino]-N-[2-hydroxy-2-(3'-hydroxyphenyl)ethyl]benzamide; 3-[(phenylsulfonyl)amino]-N-[2-hydroxy-2-(4'-hydroxy-3'-methoxyphenyl)ethyl]benzamide; 3-[(phenylsulfonyl)amino]-N-[2-(3'-hydroxy-4'-methoxyphenyl)ethyl]benzamide; 3-[(phenylsulfonyl)amino]-N-[(3'-BOC-aminomethylphenyl)methyl]benzamide; 3-[(phenylsulfonyl)amino]-N-[(3'-aminomethylphenyl)methyl]benzamide hydrochloride salt; 3-[(2-naphthalenylsulfonyl)amino]-N-[(2'-pyridyl)methyl] benzamide; 3-[(2-naphthalenylsulfonyl)amino]-N-[(3'-aminomethylphenyl)methyl]benzamide;3-[(phenylsulfonyl) amino]-N-(4-aminobutyl)benzamide; 3-[(3'-aminophenylsulfonyl)amino]-N-[4'-[(N',N'-dimethylamino)phenyl]methyl]benzamide; 3-[(2-naphthalenylsulfonyl) amino]-N-(5-aminopentyl)benzamide; and 3-[(2-naphthalenylsulfonyl)amino]-N-(8-aminooctyl)benzamide.

The term "alkyl" as employed herein includes both straight and branched chain radicals of up to 12 carbons, preferably 1–8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various branched chain isomers thereof.

The term "substituted alkyl" as employed herein includes alkyl groups as defined above that have one, two or three halo substituents, or one $C_{6-10}$aryl, $C_{1-6}$alkyl($C_{6-10}$)aryl, halo($C_{6-10}$)aryl, $C_{3-8}$cycloalkyl, $C_{1-6}$alkyl($C_{3-8}$)cycloalkyl, $C_{2-8}$alkenyl, $C_{2-8}$alkynyl, hydroxy and/or carboxy.

The term "cycloalkyl" as employed herein includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "aralkyl" as employed herein refers to aryl groups as defined above that are attached to a $C_{1-6}$alkyl group.

The term "heterocyclic group" or "heterocycle" as used herein refers to groups having 3 to 10 carbon atoms and having one or more 4, 5, 6, or 7 member saturated or unsaturated rings containing 1, 2, or 3 oxygen, nitrogen or sulfur heteroatoms (where examples of heterocyclic radicals are: tetrahydrofuran, 1,4-dioxane, 1,3,5-trioxane, pyrrolidine, piperidine, piperazine, imadazoline, isoindoline, chromane, isochromane, pyrazolidine, quinuclidine, pyridine, pyrrole, oxazole, indole, purine, pyrimidine, 1,3-dithiane, azetidine, tetrahydropyran, imidazole, thiazole, isoxazole, pyrazole, quinoline, cytosine, thymine, uracil, adenine, guanine, pyrazine, 1-methyl-1,4-dihydronicotine, picolinic acid, picoline, furoic acid, furfural, furfuryl alcohol, carbazole, isoquinoline, 3-pyrroline, thiophene, furan, hexamnethyleneimine, ϵ-caprolactone, ϵ-caprolactam, omega-thiocaprolactam, and morpholine).

The term "heteroaryl" as employed herein refers to groups having 3 to 14 ring atoms; 6, 10 or 14 π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The terms "substituted aryl" and "substituted heteroaryl" as employed herein include aryl groups and heteroaryl groups, as defined above, that include one or two substituents on the aromatic ring(s) such as $C_{1-6}$alkyl, $C_{3-8}$cycloalkyl, $C_{1-6}$alkyl($C_{3-8}$)cycloalkyl, $C_{2-8}$alkenyl, $C_{2-8}$alkynyl, cyano, amino, $C_{1-6}$alkylamino, di($C_{1-6}$) alkylamino, benzylamino, dibenzylamino, nitro, carboxy, carbo($C_{1-6}$)alkoxy, trifluoromethyl, halogen, $C_{1-6}$alkoxy, $C_{6-10}$aryl($C_{6-10}$)alkoxy, hydroxy, $C_{1-6}$alkylthio, $C_{1-6}$alkylsulfinyl, $C_{1-6}$alkylsulfonyl, $C_{6-10}$arylthio, $C_{6-10}$arylsulfinyl and/or $C_{6-10}$ arylsulfonyl.

The terms "alkoxy" or "aralkoxy" include any of the above alkyl or aralkyl groups linked to an oxygen atom.

The term "halogen" or "halo" as used herein by itself, or as part of another group, refers to chlorine, bromine, fluorine or iodine, with chlorine being preferred.

The term "monoalkylamino" as employed herein refers to the group —$NH_2$ wherein one hydrogen has been replaced by an alkyl group, as defined above.

The term "dialkylamino" as employed herein refers to the group —NH₂ wherein both hydrogens have been replaced by alkyl groups, as defined above.

The term "aminoalkyl" as employed herein refers to any of the above alkyl groups substituted by —NH₂.

The term "hydroxyalkyl" as employed herein refers to any of the above alkyl groups substituted by one or more hydroxyl moieties.

The term "BOP" as employed herein refers to benzotriazol-1-yloxytris(dimethylamino)phosphonium hexafluorophosphate.

The term "BOC" as employed herein refers to the amino-protecting group t-butoxycarbonyl.

The compounds of the present invention may be prepared by standard techniques as outlined in Scheme I.

Scheme I

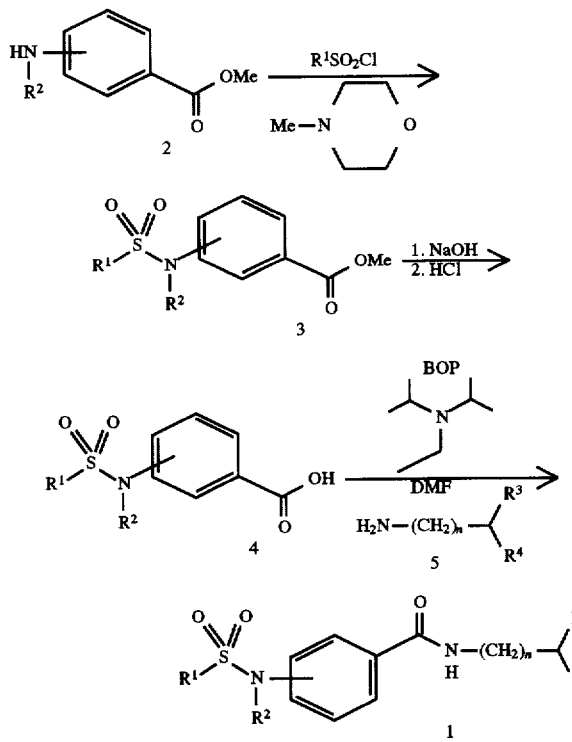

wherein $R^1$, $R^2$, $R^3$, $R^4$ and n are defined as above. Additionally, $R^4$ groups having more than one amino group may have one or more amino-protecting groups attached to the amino groups that are not to react with the carboxylic acid. Useful amino-protecting groups include benzyloxycarbonyl (CBZ) or t-butoxycarbonyl (BOC).

An aminobenzoic acid ester (that is optionally N-substituted) 2 is treated with an appropriate sulfonyl chloride under standard conditions to provide a N-sulfonylated derivative 3. Useful solvents for this step include methylene chloride, tetrahydrofuran, acetonitrile and dimethylformamide. The reaction proceeds at ambient temperature using a weak base, such as N-methylmorpholine, triethylamine or luditine. Hydrolysis of 3 with aqueous hydroxide, preferably at elevated temperature for a short time, followed by acidification with aqueous acid, such as 2N HCl, gives the corresponding carboxylic acid 4. The final product is formed by coupling the carboxylic acid 4 with an appropriate amine (or diamine of which one amino group is protected) 5 using well-known peptide coupling procedures. Reagents for the coupling step include, most preferably, Castro's reagent (BOP)/diisopropylethylamine, or alternatively, hydroxybenzotriazole (HOBT), hydroxysuccinimide, 1,3-dicyclocarbodiimide (DCC), carbonyldiimidazole (CDI), isobutylchloroformate/NEt₃, or diphenylphosphorylazide (DPPA)/NEt₃.

The compounds of the present invention where X is —CH₂— are synthesized by reductive amination of the appropriate benzaldehyde derivative employing an appropriate amine 5.

Compounds having the arylsulfonylamino moiety in the ortho- or para- position may be formed by employing commercially available anthranilic acid methyl ester or methyl p-aminobenzoate in place of methyl 3-aminobenzoate.

The compounds of the present invention are distinguished by their ability to preferentially inhibit factor Xa in comparison to thrombin and/or plasmin. As factor Xa inhibitors, the compounds of the present invention inhibit thrombin production. Therefore, the compounds are useful for the treatment or prophylaxis of states characterized by abnormal venous or arterial thrombosis involving either thrombin production or action. These states include, but are not limited to: deep vein thrombosis; disseminated intravascular coagulopathy that occurs during septic shock, viral infections, and cancer; myocardial infarction; stroke; coronary artery bypass; hip replacement; and thrombus formation resulting from either thrombolytic therapy or percutaneous transluminal coronary angioplasty (PCTA). The compounds of the present invention may also be used as an anticoagulant in extracorporeal blood circuits. By virtue of the effects of both factor Xa and thrombin on a host of cell types, such as smooth muscle cells, endothelial cells and neutrophils, the compounds of the present invention find additional use in the treatment or prophylaxis of adult respiratory distress syndrome; inflammatory responses, such as edema; reperfusion damage; atherosclerosis; and restenosis following an injury such as balloon angioplasty, atherectomy, and arterial stent placement.

The compounds of the present invention may be useful in treating neoplasia and metastasis, as well as neurodegenerative diseases, such as Alzheimer's disease and Parkinson's disease.

The compounds of the present invention may be used in combination with thrombolytic agents, such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

For medicinal use, the pharmaceutically acceptable acid addition salts, those salts in which the anion does not contribute significantly to toxicity or pharmacological activity of the organic cation, are preferred. The acid addition salts are obtained either by reaction of an organic base of Formula I with an organic or inorganic acid, preferably by contact in solution, or by any of the standard methods detailed in the literature available to any practitioner skilled in the art. Examples of useful organic acids are carboxylic acids such as maleic acid, acetic acid, tartaric acid, propionic acid, fumaric acid, isethionic acid, succinic acid, palmoic acid, cyclamic acid, pivalic acid and the like. Useful inorganic acids are hydrohalide acids, such as HCl, HBr, HI, sulfuric acid, phosphoric acid and the like.

The compounds of the present invention may be administered in an effective amount within the dosage range of about 0.1 to about 500 mg/kg, preferably between 0.1 to 10 mg/kg body weight, on a regimen in single or 2–4 divided daily doses.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically. The pharmaceutical preparations of the present invention are manufactured in a mariner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, that may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts and alkaline solutions. Especially preferred alkaline salts are ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

Preparation of Methyl 3-Aminobenzoate (11)

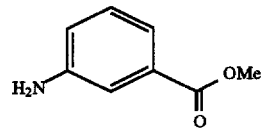

A mixture of methyl 3-nitrobenzoate (18.1 g, 0.10 mmol) in ethanol/tetrahydrofuran (THF) (9:1), and 1.8 g of 10% Pd/C was hydrogenated at atmospheric pressure and ambient temperature for 24 hr. The reaction mixture was filtered through Celite (Celite is a registered trademark of the Johns-Manville Product Corporation for diatomaceous earth) and washed with ethanol. The solvent was removed in vacuo to give the title compound as a pale yellow solid (14.7 g; 97% yield) that was used without further purification in the next reaction. $^1$H-NMR (200 MHz; CDCl$_3$) δ 7.43 (d, 1H, J=7.6 Hz), 7.35 (t, 1H, J=2.3 Hz), 7.25 (d, 1H, J=2.3 Hz), 7.19 (d, 1H, J=7.7 Hz), 3.89 (s, 3H), 3.7 ppm (bs, 2H).

EXAMPLE 2

Methyl 3-((2-Naphthalenyl)sulfonyl)aminobenzoate (12)

To 5.0 g (33 mmol) of the methyl 3-aminobenzoate (11) prepared in Example 1 in 70 mL of methylene chloride containing 4.0 mL (36 mmol) of N-methylmorpholine was added 7.49 g (33 mmol) of 2-naphthalenesulfonyl chloride. After stirring at room temperature overnight, the reaction mixture was quenched with 1N HCl (100 mL). The suspension was dissolved in ca. 250 mL of THF and enough ether was added to induce phase separation. The organic extract was washed with saturated sodium chloride solution (2×). The organic phase was dried (MgSO$_4$), and concentrated to give 11.0 g (97% yield) of the title compound as a pale yellow solid: $^1$H-NMR (200 MHz; DMSO-d$_6$) δ 8.46 (s, 1H), 8.13 (t, 2H), 7.99 (d, 1H), 7.55–7.75 (m, 5H), 7.43 (dd, 21H), 7.38 (d, 1H), 3.79 ppm (s, 3H).

EXAMPLE 3

Preparation of 3-((2-Naphthalenyl)sulfonyl) aminobenzoic acid (13)

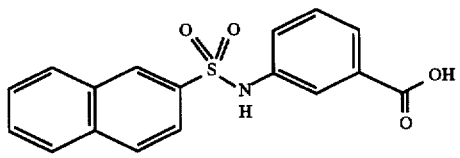

A solution of 10.8 g (31.7 mmol) of methyl 3-((2-naphthalenyl)sulfonyl)aminobenzoate (12) as prepared in Example 2 in 100 mL of 1N NaOH was stirred at 50° C. for 20 min. The reaction mixture was quenched with excess 2N HCl, diluted with tetrahydrofuran to dissolve the suspension. Ether was added to induce phase separation. The organic extract was dried (MgSO$_4$) and the solvent removed in vacuo. Trituration from ether/tetrahydrofuran/hexane gave 10.0 g of the title compound: $^1$H-NMR (200 MHz, DMSO-d$_6$) δ 8.45 (s, 1H), 8.13 (t, 2H), 7.99 (d, 1H), 7.54–781 (m, 5H), and 7.77–7.43 ppm (m, 2H). Mass spectrum (MALDI-TOF) calcd. for C$_{17}$H$_{13}$NO$_4$S: 328.1 (M+H) and 350.0 (M+Na). Found: 328.7 (M+H), 349.8 (M+Na).

EXAMPLE 4

Preparation of 3-[(2-Naphthalenylsulfonyl)amino]-N-[2-hydroxy-2-(3'-hydroxyphenyl)ethyl]benzamide (14)

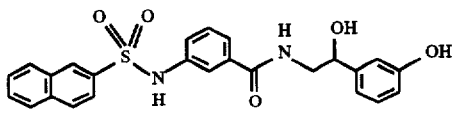

To 160 mg (0.469 mmol) of 3-((2-naphthalenyl)sulfonyl) aminobenzoic acid (13) as prepared in Example 3 in 2 mL of N,N-dimethylformamide was added sequentially 221 mg (0.50 mmol) of Castro's Reagent (benzotriazole-1-yloxytris (dimethylamino)phosphonium hexafluorophosphate) and 500 μL (2.87 mmol) of N,N-diisopropylethylamine. The 94.8 mg (0.50 mmol) of ±-norepinephrine HCl was added. After stirring for 20 rain, the reaction mixture was quenched with 2N HCl (5 mL) and then was extracted into ethyl acetate (2×4 mL). The organic phase was washed with saturated NaHCO$_3$, dried (Na$_2$SO$_4$) and concentrated to give 150 mg of the title compound as a foam. NMR (DMSO-d$_6$; 300 MHz) δ 10.56 (s, 1H), 9.31 (s, 1H), 8.45 (m 2H), 8.11 (t, 2H), 8.00 (d, 1H), 7.77 (dd, 1H, J=(1.8, 8.7 Hz) 7.59–7.72 (m, 3H), 7.42–7.47 (m, 1H), 7.22–7.30 (m, 2H), 7.08 (t, 1H), 677 (s, 1H), 6.72 (d, 1H, J=7.6 Hz), 6.62 (dd, 1H, J=1.8, 7.7 Hz), 5.40 (d, 1H), J=4.2 Hz), 4.63 (pentet, 1H), and 3.14–3.23 ppm (m, 1H). Mass spectrum (MALDI-TOF) calcd. for C$_{25}$H$_{22}$N$_2$O$_5$S: 485.1 (M+Na). Found: 484.9.

EXAMPLE 5

Preparation of 3-[(2-Naphthalenylsulfonyl)amino]-N-[2-hydroxy-2(4'-hydroxyphenyl)ethyl]benzamide (15)

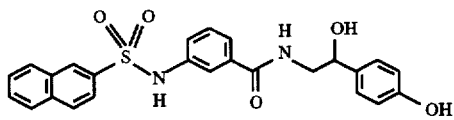

The title compound was prepared in an identical fashion to Example 4 using 94.8 mg (0.5 mmol) of ±-octopamine HCl. Purification was achieved by passing the crude reaction product through 15 mL of silica gel using elutions of methylene chloride/ethyl acetate (2:1 to 1:1) to afford 122 mg of the title compound as a foam: NMR (DMSO-d$_6$; 300 MHz) δ 10.56 (s, 1H), 9.26 (s, 1H), 8.44 (s, 1H), 8.36 (t, 1H, J=5 Hz), 8.10 (t, 2H), J=9 Hz), 8.00 (d, 8 Hz), 7.78 (dd, 1H, J=1.7 Hz, 8 Hz), 7.61–7.72 (m, 3H), 7.39–7.44 (m, 1H), 7.24–7.29 (m, 2H), 7.12 (d, 2H, J=7 Hz), 6.69 (d, 2H, J=7 Hz), 5.28 (d, 1H, J=5 Hz, 4.60), 4.03 (q, 1H, J=7 Hz), 3.16–2.52 ppm (m, 1H).

EXAMPLE 6

Preparation of 3-[(2-Naphthalenylsulfonyl)amino]-N-[4'-[N',N'-dimethylamino)phenyl]methyl]benzamide (16)

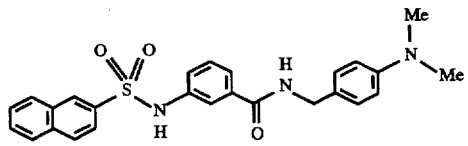

To a solution of 160 mg (0.469 mmol) of 3-((2-naphthalenyl)sulfonyl)aminobenzoic acid (13) as prepared in Example 3, in 1 mL of N,N-dimethylformamide was added 1 mL of 0.5M (0.5 mmol) of Castro's reagent (benzotriazole-1-yloxytris(dimethylamino)phosphonium hexafluorophosphate) in N,N-dimethylformamide and then 500 μL of N,N-diisopropylethylamine. After 5 min, the solution was transferred dropwise to a solution of 104 mg (0.47 mmol) of 4-(dimethylamino)benzylamine dihydrochloride salt in N,N-dimethylformamide. After 30 min, the reaction mixture was quenched with 10 mL of saturated NaHCO$_3$, and extracted into ethyl acetate (3 mL). The organic phase was washed with sat. NaHCO$_3$ (4×5 mL), concentrated in vacuo, and crystallized from ethyl acetate/hexane/methylene chloride/ether to give 90 mg of the title compound: NMR (DMSO-d$_6$; 300 MHz) δ 10.55 (s, 1H), 8.82 (t, 1H, J=6 Hz), 8.44 (d, 1H, J=1 Hz), 8.0–9 (t, 2H), 7.99 (d, 1H, J=7 Hz), 7.77 (dd, 1H, J=1, 8 Hz), 7.61–7.72 (m, 3H), 7.44–7.48 (m, 1H), 7.22–7.29 (m, 2H), 7.09 (d, 2H, J=9 Hz), 6.65 (d, 2H, J=9 Hz), 427 (d, 2H, J=6 Hz), 2.84 ppm (s, 6H).

EXAMPLE 8

Preparation of Methyl 3-(Phenylsulfonyl) aminobenzoate (18)

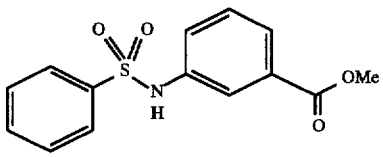

To 4.6 g (3.03 mmol) of the methyl 3-aminobenzoate prepared in Example 1 in 30 mL of methylene chloride containing 4.0 mL (36 mmol) of N-methylmorpholine was added 4.0 mL (33 mmol) of benzenesulfonyl chloride. After stirring at room temperature for 1 hr the reaction mixture was quenched with water (100 mL). The suspension was dissolved in ethyl acetate/ether combination. The organic phase was washed sequentially with 2N HCl and then sodium bicarbonate. The organic phase was dried (MgSO$_4$), and concentrated and triturated from ethyl acetate/hexane ether to give 8.0 g (90%) of the title compound as a colorless solid: NMR (DMSO-d$_6$; 300 MHz) δ 10.58 (s, 1H), 7.75–7.84 (m, 3H), 7.52–7.72 (m, 4H), 7.35–7.45 (m, 2H), and 3.82 ppm (s, 3H).

EXAMPLE 9

Preparation of 3-(Phenylsulfonyl)aminobenzoic Acid (19)

To 8.0 g (27 mmol) of methyl 3-aminobenzoate was added 60 mL of 2N NaOH. After stirring for 30 min at ambient temperature, the reaction mixture was washed with ether and then acidified with 2.5N HCl. The reaction mixture was extracted into ethyl acetate, dried (MgSO$_4$), and concentrated to give 6.62 g (89%) after washing the solid thoroughly with ether/hexane mixture: NMR (DMSO-d$_6$; 300 MHz) δ 13.0 (bs, 1H), 10.53 (s, 1H), 7.75–7.84 (m, 2H), 7.69 (t, 1H), 7.52–7.66 (m, 4H), 7.28–7.42 ppm (m, 2H). Mass spectrum (MALDI-TOF) calcd. for C$_{13}$H$_{11}$NO$_4$S: 300.0 (M+Na). Found: 299.7.

EXAMPLE 10

Preparation of 3-[(Phenylsulfonyl)amino]-N-[(4-hydroxy-3-methoxyphenyl)methyl]benzamide (20)

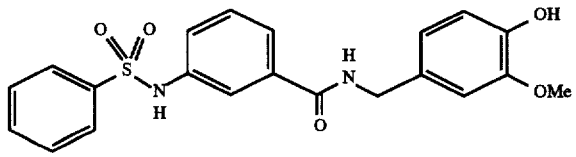

To 139 mg (0.5 mmol) of 3-(phenylsulfonyl) aminobenzoic acid as prepared in Example 9 in 1 mL of N,N-dimethylformamide was added sequentially 1 mL of 0.5M (0.5 mmol) of Castro's reagent (benzotriazole-1-yloxytris(dimethylamino)phosphonium hexafluorophosphate) in N,N-dimethylformamide and then 500 µL of N,N-diisopropylethylamine. After 5 min, 95 mg (0.5 mmol) of 4-hydroxy-3-methoxybenzylamine HCl was added. After 30 min, the reaction mixture was quenched with 7 mL of 2N HCl, extracted into ethyl acetate (2×2 mL), washed with water (3×4 mL) and then sat. NaHCO$_3$ (1×4 mL). The organic phase was passed through a Waters solid phase extraction column (5 g silica gel) onto which was added Na$_2$SO$_4$ to act a drying agent. Elution with ethyl acetate gave the title compound: NMR (DMSO-d$_6$; 300 MHz) δ 10.46 (s, 1H), 8.88 (t, 1H), 8.84 (s, 1H), 7.74–7.81 (m, 3H), 7.50–7.70 (m, 6H), 7.30 (t, 1H) 7.22 (d, 1H), 6.87 (s, 1H), 6.69 (t, 2H), 4.31 (d, 2H), 3.73 ppm (s, 3H). Mass spectrum (MALDI-TOF; gentisic acid matrix) calcd. for C$_{27}$H$_{20}$N$_2$O$_5$S: 435.1 (M+Na). Found: 435.0.

EXAMPLE 11

Preparation of 3-[(Phenylsulfonyol)amino]-N-[2-hydroxy-2-(3'-hydroxyphenyl)ethyl]benzamide (21)

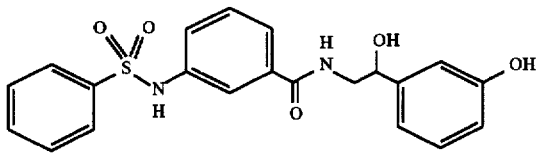

The title compound (115 mg) was prepared using the identical procedure described in Example 10 and ±-norepinephrine (95 mg; 0.5 mmol) as the coupling amine: NMR (DMSO-d$_6$; 300 MHz) δ 10.46 (s, 1H), 9.31 (s, 1H), 8.46 (t, 1H, J=5 Hz), 7.70–7.8 ((m, 2H), 7.41–7.7 (m, 5H), 7.30 (t, 1H), 7.22 (d, 1H), 7.10 (t, 1H), 6.79 (s, 1H), 6.74 (d, 1H), 6.63 (dd, 1H), 5.41 (d, 1H, J=4 Hz), 4.64 (pentet, 1H), 3.36–3.48 (m, 1H), and 3.15–3.28 ppm (m, 1H). Mass spectrum (MALDI-TOF; gentisic acid matrix) calcd. for C$_{21}$H$_{20}$N$_2$O$_5$S: 435.1 (M+Na), 451.1 (M+K). Found: 435.0, 451.2.

Example 12

Preparation of 3-[(Phenylsulfonyl)amino]-N-[2-hydroxy-2-(4'-hydroxy-3'-methoxyphenyl)ethyl]benzamide (22)

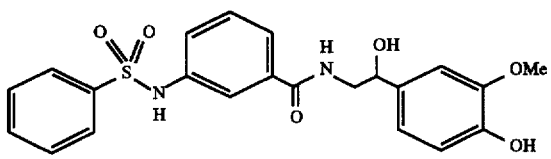

The title compound was prepared using the identical procedure described in Example 10 and ±-normetanephrine (110 mg; 0.5 mmol) as the coupling amine: NMR (DMSO-d$_6$; 300 MHz) δ 10.45 (s, 1H), 8.81 (s, 1H), 8.37 (t, 1H), 7.71–7.8 (m, 2H), 7.45–7.68 (m, 5H), 7.29 (t, 1H), 7.21 (d, 1H) 6.88 (s, 1H), 6.71 (s, 2H), 5.33 (d, 1H), 4.63 (pentet, 1H), 3.72 (s, 3H), and 3.2–3.4 ppm (m, 2H). Mass spectrum (MALDI-TOF; gentisic acid matrix) calcd. for C$_{22}$H$_{22}$N$_2$O$_6$S: 463.1 (M+Na), 481.1 (M+K). Found: 464.5, 480.5.

EXAMPLE 13

Preparation of 3-[(Phenylsulfonyl)amino]-N-[2-(3'-hydroxy -4'-methoxyphenyl)ethyl]benzamide (23)

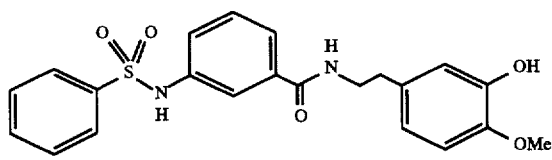

The title compound was prepared using the identical procedure described in Example 10 and 4-O-methyldopamine (102 mg; 0.5 mmol) as the coupling amine: NMR (DMSO-$d_6$; 300 MHz) δ 10.45 (s, 1H), 8.85 (s, 1H), 8.48 (s, 1H), 7.74–7.78 (m, 2H), 7.4–7.7 (m, 5H), 7.30 (t, 1H), 7.21 (d, 1H), 6.81 (d, 1H, J=8 Hz), 6.65 (d, 1H, J=2 Hz), 6.57 (dd, 1H), 3.71 (s, 3H), 3.26–3.47 (m, 2H), 2.64 ppm (t, 1H). Mass spectrum (MALDI-TOF; gentisic acid matrix) calcd. for $C_{22}H_{22}N_2O_5S$: 449.1 (M+Na). Found: 448.9.

EXAMPLE 14

Preparation of N-BOC-m-xylylenediamine (24)

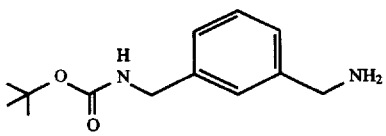

To 4.5 g (0.033 mol) of m-xylylenediamine in 100 mL of THF containing 6 mL (0.047 mmol) of N,N-diisopropylethylamine was added 3.0 g of di-t-butyldicarbonate. The reaction mixture was stirred for 10 min, quenched with 2N NaOH, extracted into methylene chloride. The organic phase was washed with water (5×), and then acidified with 10% citric acid. The aqueous phase was basified with 2N NaOH and then extracted with methylene chloride. The organic phase was dried ($K_2CO_3$) and concentrated to give 1.0 g of the title compound: NMR (CDCl$_3$; 300 MHz) δ 7.31 (d, 1H), 7.27 (d, 1H), 7.23 (s, 1H), 7.18 (t, 1H), 4.87 (bs, 1H), 4.32 (d, 2H), 3.86 (s, 2H), 1.45 ppm (s, 9H).

EXAMPLE 15

Preparation of 3-[(Phenylsulfonyl)amino]-N-[(3'-BOC-aminomethylphenyl)methyl]benzamide (25)

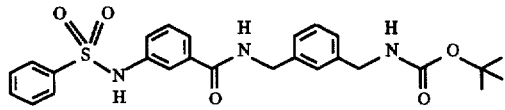

The title compound (45 mg) was prepared using the identical procedure described in Example 10 using 118 mg of the amine (24) of Example 14 as the coupling amine. Purification was achieved by chromatography through a 5 g Waters solid phase extraction column (silica gel) using ethyl acetate elution: NMR (DMSO-$d_6$; 300 MHz) δ 10.5 (bs, 1H), 9.0 (t 1H), 7.0–7.8 (m, 13H), 4.41 (d, 2H), 4.09 ppm (d, 2H). Mass spectrum (MALDI-TOF; gentisic acid matrix) calcd. for $C_{26}H_{29}N_3O_5S$: 496.2 (M+H), 518.2 (M+Na), 534.1 (M+K). Found: 496.9, 517.9, 534.5.

EXAMPLE 16

Preparation of 3-[(Phenylsulfonyl)amino]-N-[(3'-aminomethylphenyl)methyl]benzamide hydrochloride salt (26)

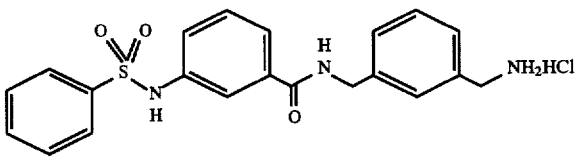

The compound obtained in Example 15 (35 mg) was treated with 1 mL of 4N HCl in dioxane for 1 hr. Concentration and trituration from ether/methylene chloride/methanol gave 15 mg of the title compound: NMR (DMSO-$d_6$; 300 MHz) δ 10.5 (bs, 1H), 9.07 (t, 1H), 8.22 (bs, 2H), 7.0–7.8 (m, 13H), 4.44 (d, 2H), and 4.00 ppm (d, 2H). Mass spectrum (MALDI-TOF; gentisic acid matrix) calcd. for $C_{21}H_{21}N_3O_3S$: 396.1 (M+H). Found: 396.0.

EXAMPLE 17

Preparation of 3-[(2-Naphthalenylsulfonyl)amino]-N-[(2'-pyridyl)methyl]benzamide (27)

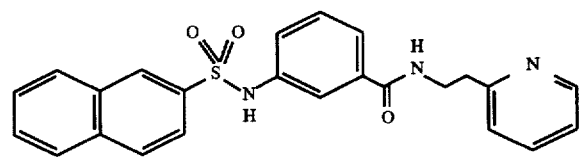

3-((2-Naphthalenyl)sulfonyl)aminobenzoic as prepared in Example 3 (164 mg, 0.5 mmol), Castro's reagent (benzotriazole- 1 -yloxytris(dimethylamino)phosphonium hexafluorophosphate) (221 mg, 0.5 mmol), 2-(2-aminoethyl)pyridine (73 mg, 0.6 mmol) and triethylamine (0.2 mL) were mixed in dry DMF (5 mL) and stirred at room temperature for 3 hours. The mixture was dissolved in ethyl acetate (100 mL) and washed with saturated NaHCO$_3$ (2×50 mL), brine (2×50 mL) and dried over Na$_2$SO$_4$. Evaporation of the solvent gave the title compound (185 mg, 86%) as white foam: $^1$H-NMR (300 MHz, CDCl$_3$/CD$_3$OD): δ 3.15(t, 2H), 3.72 (t, 2H), 7.27 (t, 1H), 7.43 (m, 5H), 7.59 (m, 2H), 7.78 (dd, 1H), 7.87 (m, 4H), 8.37 (s, 1H), 8.47 (d, 1H). Mass spectrum (MALDI-TOF) calcd. for $C_{24}H_{21}N_3O_3S$ : 456.5 (M+Na), Found: 456.5.

EXAMPLE 18

Preparation of 3-[(2-Naphthalenylsulfonyl)amino]-N-[(3'-aminomethylphenyl)methyl]benzamide (28)

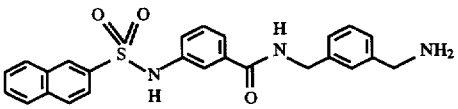

3-((2-Naphthalenyl)sulfonyl)aminobenzoic acid as prepared in Example 3 (230 mg, 0.7 mmol), Castro's reagent (benzotriazole-1-yloxytris(dimethylamino)phosphonium hexafluorophosphate) (310 mg, 0.7 mmol), m-xylylenediamine (680 mg, 5 mmol) and triethylamine (0.3 mL) were mixed in dry DMF (5 mL) and stirred at room temperature for 3 hours. The mixture was dissolved in ethyl acetate (100 mL) and washed with saturated NaHCO$_3$ (2×50 mL) and brine (2×50 mL). The organic phase was then washed with 1N HCl (4×50 mL) and the acid solution was neutralized to pH8 and extracted with ethyl acetate (3×50 mL). The combined ethyl acetate extracts were washed with brine (2×50 mL), dried over Na$_2$SO$_4$ and evaporated to give the title compound (130 mg, 42%) as white solid: $^1$H-NMR (300 MHz, DMSO-d$_6$): δ 3.82 (s, 2H), 4.40 (d, 2H), 7.27 (m, 5H), 7.42 (t, 1H), 7.65 (m, 3H), 7.78 (dd, 1H), 7.97 (d, 1H), 8.05 (d, 1H), 8.08 (d, 1H), 8.42 (s, 1H), 8.95 (t, 1H). Mass spectrum (MALDI-TOF) calcd. for C$_{25}$H$_{23}$N$_3$O$_3$S: 468.5 (M+Na$^+$), Found: 468.0.

EXAMPLE 19

Preparation of 3-[(Phenylsulfonyl)amino]-N-(4-aminobutyl)benzamide (29)

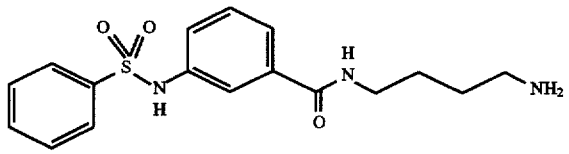

3-(Phenylsulfonyl)aminobenzoic acid as prepared in Example 9 (139 mg, 0.5 mmol), Castro's reagent (benzotriazole-1-yloxytris(dimethylamino)phosphonium hexafluorophosphate) (221 mg, 0.5 mmol), tert-butyl 4-aminobutylaminocarboxylate (100 mg, 0.6 mmol) and triethylamine (0.2 mL) were mixed in dry DMF (5 mL) and stirred at room temperature for 3 hours. The mixture was dissolved in ethyl acetate (100 mL) and washed with saturated NaHCO$_3$ (2×50 mL), brine (2×50 mL) and dried over Na$_2$SO$_4$. After evaporation of the solvent, the residue was mixed with 1:1 trifluoroacetic acid (TFA):CH$_2$Cl$_2$ (10 mL), stirred at room temperature for 2 hours and the solvent evaporated to give the title compound (140 mg, 81%) as the TFA salt. $^1$H-NMR (300 MHz, DMSO-d$_6$): δ 1.17 (m, 4H), 2.79 (t, 2H), 3.23 (d, 2H), 7.23 (d, 1H), 7.30 (t, 1H), 7.57 (m, 5H), 7.60 (d, 2H), 8.50 (t, 1H). Mass spectrum (MALDI-TOF) calcd. for C$_{17}$H$_{21}$N$_3$O$_3$S: 370.4 (M+Na), Found: 370.7.

EXAMPLE 20

Preparation of 3-((3-Nitrophenyl)sulfonyl) aminobenzoic acid (30)

To 1.51 g (10 mmol) of the methyl 3-aminobenzoate prepared in Example 1 in 40 mL of methylene chloride containing 2 mL of N-methylmorpholine was added 2.21 g (10 mmol) of 3-nitrobenzenesulfonyl chloride. After stirred at room temperature for 3 hours, methylene chloride (200 mL) was added and washed with saturated NaHCO$_3$ (2×50 mL), 1N HCl (2×50 mL) and brine (2×50 mL) and dried over Na$_2$SO$_4$. After evaporation of the solvent, the residue was dissolved in THF (50 mL), 2N NaOH (10 mL) was added and the mixture heated to 60° C. for 2 hours. After neutralization with 1N HCl, the mixture was extracted with ethyl acetate (4×50 mL) and the organic phase was washed with brine (2×50 mL), dried over Na$_2$SO$_4$ and evaporated to give 3.05 g (94%) of the title compound as a white solid: $^1$H-NMR (300 MHz, DMSO-d$_6$): δ 7.38 (m, 2H), 7.65 (t, 1H), 7.70 (s, 1H), 7.87 (t, 1H), 8.13 (dd, 1H), 8.47 (dd, 1H), 8.50 (t, 1H), 10.81 (s, 1H), 13.11 (s, 1H).

EXAMPLE 21

Preparation of 3-[(3'-Aminophenylsulfonyl)amino]-N-[4'-[(N', N'-dimethylamino)phenyl]methyl] benzamide (31)

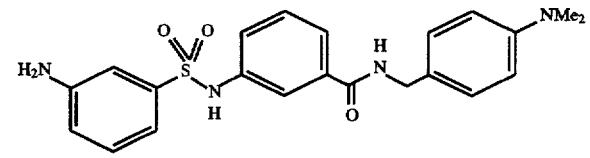

3-((3-Nitrophenyl)sulfonyl)aminobenzoic acid as prepared in Example 20 (322 mg, 1.0 mmol), Castro's reagent (benzotriazole-1-yloxytris(dimethylamino)phosphonium hexafluorophosphate) (442 mg, 1.0 mmol), 4-dimethylaminobenzylamine dihydrochloride (223 mg, 1.0 mmol) and N,N-diisopropylethylamine (0.4 mL) were mixed in dry DMF (8 mL) and stirred at room temperature for 3 hours. The mixture was dissolved in ethyl acetate (200 mL) and washed with saturated NaHCO$_3$ (2×50 mL), brine (2×50 mL) and dried over Na$_2$SO$_4$. Evaporation of the solvent gave the title compound (410 mg, 89%) as white solid. $^1$H-NMR (300 MHz, DMSO-d$_6$): δ 3.06 (s, 6H), 4.42 (d, 2H), 7.28 (d, 1H), 7.35 (m, 3H), 7.52 (m, 4H), 7.86 (t, 1H), 8.15 (d, 1H), 8.48 (m, 2H), 9.13 (t, 1H), 10.82 (s, 1H). Mass spectrum (MALDI-TOF) calcd. for C$_{22}$H$_{22}$N$_4$O$_3$S: 477.5 (M+Na), Found: 477.2.

The above compound (228 mg, 0.5 mmol) was dissolved in THF (10 mL) and ethanol (10 mL), palladium on carbon (10%, 20 mg) was added to the solution and the mixture hydrogenated at atmospheric pressure for 4 hours. The mixture was then filtered through Celite and washed with THF and the combined filtrates evaporated to dryness to give the title compound (200 mg, 94%) as a white solid. $^1$H-NMR (300 MHz, DMSO-d$_6$): δ 3.05 (s, 6H), 4.45 (d, 2H), 7.20–7.90 (m, 12H), 9.15 (s, 1H), 10.48 (s, 1H). Mass spectrum (MALDI-TOF) calcd. for C$_{22}$H$_{24}$N$_4$O$_3$S: 447.5 (M+Na), Found: 446.9.

EXAMPLE 22

Preparation of 3-[(2-Naphthalenylsulfonyl)amino]-N-(5-aminopentyl)benzamide (32)

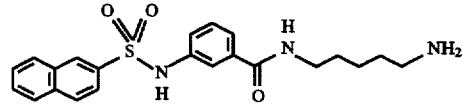

The title compound was prepared from the identical procedure of Example 6 using 280 µL (2 mmol) of 1,5-diaminopentane. Work up consisted of the following steps. The ethyl acetate extract was acidified with 2N HCl. The aqueous phase was treated with excess sat. NaHCO$_3$ and then extracted with ethyl acetate. The organic phase was washed with saturated NaHCO$_3$, dried (Na$_2$SO$_4$), and concentrated to provide 43 mg of the title compound as a hardened glass: NMR (DMSO-d$_6$, 300 MHz) δ 8.44 (d, 1H, 1.4 Hz), 8.38 (t, 1H, J=5 Hz), 8.10 (t, 2H, J=8 Hz), 7.99 (t, 1H, J=8 Hz), 7.77 (dd, 1H, J=1.8, 8 Hz), 7.60–7.72 (m, 5H), 7.41–7.45 (m, 1H), 7.23–7.30 (m, 2H), 3.19 (q, 2H), 1.43–1.57 (m, 4H), 1.14–1.34 ppm (m, 4H). Mass spectrum (MALDI-TOF) calcd. for $C_{22}H_{25}N_3O_3S$: 434.2 (M+Na). Found: 434.7

EXAMPLE 23

Preparation of 3-[(2-Naphthalenylsulfonyl)amino]-N-(8-(aminooctyl)benzamide (33)

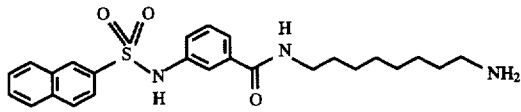

The title compound (13 mg) was prepared from the identical procedure of Example 22 using 340 mg of 1,8-diaminooctane. Purification of the product was achieved by chromatography on silica gel ($CH_2Cl_2$/MeOH/$NH_4OH$ (85:10:5, dried over $Na_2CO_3$)): NMR (DMSO-$d_6$, 300 MHz) δ 8.34 (s, 1H), 8.19 (t, 1H, J=5 Hz), 8.01–8.05 (m, 1H), 7.91–7.97 (m, 2H), 7.76 (dd, 1H), 7.55–7.63 (m, 2H), 7.35 (s, 1H), 7.02–7.14 (m, 5H), 3.16 (q, 2H), 2.72 (q, 2H), 1.47 ppm (q, 2H). Mass spectrum (MALDI-TOF) calcd. for $C_{25}H_{31}N_3O_3S$: 454.2 (M+H), 476.2 (M+Na). Found: 454.0, 476.1.

EXAMPLE 24

Preparation of 3-[(phenylsulfonyl)amino]-N-[3-quinuclidinyl]benzamide (34)

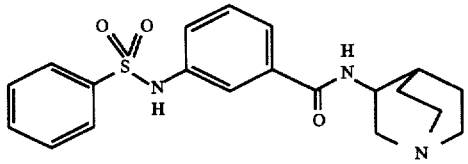

3-(Phenylsulfonyl)aminobenzoic acid as prepared in Example 9 (139 mg, 0.5 mmol), Castro's reagent (benzotriazole-1-yloxytris(dimethylaminophosphonium hexafluorophosphate) (221 mg, 0.5 mmol), 3-aminoquinuclidine hydrochloride (100 mg, 0.5 mmol) and N,N-diisopropylethylamine (0.5 mL) were dissolved in dry DMF (2 mL) and the reaction mixture was stirred at room temperature overnight. The reaction mixture was diluted with saturated $NaHCO_3$ and extracted with ethyl acetate (3×). The combined ethyl acetate was washed with brine and dried over $Na_2SO_4$. After evaporation, the residue was purified by silica gel chromatography using 86% methylene chloride and 14% methanol containing 0.25 mL of acetic acid to give 65 mg (34% yield). $^1$H-NMR (300 MHz; DMSO-d6): d 1.69–2.14 (m,5H), 3.07–3.35 (m,6H), 3.63 (t, 1H, J=12 Hz), 4.22 (m, 1H), 7.23–7.77 (m, 9H), 8.53 (d, 1H, J=6 Hz). Mass spectrum (MALDI-TOF) calcd. for $C_{20}H_{23}N_3O_3S$: 386.2 (M+H). Found: 386.2.

EXAMPLE 25

In Vitro Inhibition of Purified Enzymes

The ability of the compounds of the present invention to act as inhibitors of thrombin, factor Xa and plasmin catalytic activity was assessed by determining the concentration that inhibited enzyme activity by 50% using purified human enzymes. The concentration of added inhibitor that caused a 50% decrease in the initial rate of hydrolysis was defined as the $IC_{50}$ value.

All assays are based on the ability of the test compound to inhibit the hydrolysis of a peptide p-nitroanilide substrate. In a typical experiment, appropriate substrate is prepared in DMSO, and diluted into an assay buffer consisting of 50 mM HEPES and 130 mM NaCl at a pH of 7.5. The final concentration for each of the substrates is listed below. All substrate concentrations are at least 10 fold lower than $K_m$ to insure inhibition is competitive. Test compounds are prepared as 1 mg/mL solutions in DMSO, and three additional 10-fold dilutions in DMSO are prepared. Enzyme solutions are prepared at the concentrations listed below in assay buffer.

In a typical $IC_{50}$ determination, into each well of a 96 well plate is pipetted 280 µL of substrate solution, 10 µL of inhibitor solution, and the plate is allowed to thermally equilibrate at 37° C. in a Molecular Devices Plate Reader for at least 10 minutes. Reactions are initiated by the addition of a 20 µL aliquot of enzyme, and the absorbance increase at 405 nm is recorded for 15 minutes. Data corresponding to less than 10% of the total substrate hydrolysis is used in the calculations. The ratio of the velocity (rate of the change in absorbance as a function of time) for a sample containing no inhibitor is divided by the velocity of a sample containing inhibitor, and is plotted as a function of inhibitor concentration. The inverse of the slope is the concentration of inhibitor which produces a 50% decrease in activity of the enzyme. This concentration is referred to as the $IC_{50}$.

Thrombin

Thrombin activity was assessed as the ability to hydrolyze the substrate N-benzoyl-Phe-Val-Arg-p-nitroanilide (Bz-Phe-Val-Arg-pNa), and was obtained from Sigma Chemical Company (St. Louis, Mo.). Substrate solutions were prepared at a concentration of 60 µM (60 µM<<$K_m$=1.2 mM) in assay buffer. Final DMSO concentration was 0.3%. Purified human α-thrombin was obtained from Enzyme Research Laboratories, Inc., and was diluted into assay buffer to a concentration of 1.2 µM. Final reagent concentrations were: [thrombin]=36 nM, [Bz-Phe-Val-Arg-pNa]=66 µM, [inhibitor]=60 to 0.06 µM.

Factor Xa

Factor Xa activity was assessed as the ability to hydrolyze the substrate Bz-Ile-Glu-Gly-Arg-pNa, and was obtained from Sigma. Substrate solutions were prepared at a concentration of 26 µM (26 µM<<$K_m$=1.3 mM) in assay buffer. Final DMSO concentration was 0.3%. Activated factor Xa was obtained from Enzyme Research Laboratories, Inc., and was diluted into assay buffer to a concentration of 1.2 µM. Final reagent concentrations were: [Factor Xa]=10 nM, [Bz-Ile-Glu-Gly-Arg-pNa]=26 µM, [inhibitor]=60 to 0.06 µM.

Plasmin

Plasmin activity was assessed as the ability to hydrolyze the substrate Tos-Gly-Pro-Lys-pNa, and was obtained from Sigma. Substrate solutions were prepared at a concentration of 22 µM (22 µM<<$K_m$=240 µM) in assay buffer. Final DMSO concentration was 0.3%. Purified human plasmin was obtained from Enzyme Research Laboratories Inc. and was diluted into assay buffer to a concentration of 1.2 µM. Final reagent concentrations were: [plasmin]=15 nM, [Bz-Ile-Glu-Gly-Arg-pNa]=26 µM, [inhibitor]=60 to 0.06 µM.

The results obtained employing compounds 14, 16, 27, 32, 20, 22 and 31 are given in Table 1.

21

TABLE 1

| Compound No. | Factor Xa Inhibition (μM) | Thrombin Inhibition (μM) | Plasmin Inhibition (μM) |
|---|---|---|---|
| 14 | 11.4 | 87.0 | 86.12 |
| 16 | 3.2 | 52.8 | 0% at 60 μM |
| 27 | 2.0 | 294 | 0% at 60 μM |
| 32 | 7.6 | 0% at 60 μM | 0% at 60 μM |
| 20 | 19.2 | 0% at 60 μM | 5.8 |
| 22 | 20.8 | 38.3 | 0% at 60 μM |
| 31 | 16.5 | 0% at 60 μM | 15.2 |

The results indicate that the compounds of the present invention are highly selective and potent inhibitors of factor Xa.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound having the Formula I:

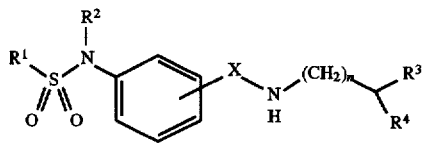

or a pharmaceutically acceptable salt thereof;
wherein
$R^1$ is alkyl, substituted alkyl, cycloalkyl, aryl, or substituted aryl;
$R^2$ is one of hydrogen, alkyl, cycloalkyl, aryl or aralkyl;
$R^3$ is one of hydrogen, hydroxy or alkoxy;
$R^4$ is one of —$NH_2$, substituted phenyl, or a $C_{3-10}$ heterocycle selected from the group consisting of quinuclidinyl, piperidinyl, morpholinyl, pyrrolidinyl, pyridinyl, pyrimidinyl and imidazole, wherein said phenyl is substituted and said $C_{3-10}$ heterocycle is optionally substituted with one or two of halogen, hydroxy, hydroxyalkyl, alkoxy, amino, monoalkylamino, dialkylamino, aminoalkyl, monoalkylaminoalkyl, or dialkylaminoalkyl;
X is one of —$CH_2$— or —C(O)—;
n is from zero to eleven; and
wherein X is attached to the benzene ring in a position ortho-, meta- or para- to the sulfonylamino group;
provided that when $R^4$ is —$NH_2$, then $R^3$ is hydrogen and n is other than zero; further provided that when $R^3$ is hydroxy or alkoxy, then $R^4$ is other than —$NH_2$, and n is other than zero;
further provided that when $R^2$ is hydrogen or methyl, while $R^3$ is hydrogen, $R^4$ is pyridyl, X is —C(O)—, and n is zero or one, then $R^1$ is other than unsubstituted phenyl.

2. The compound of claim 1, wherein
$R^1$ is optionally substituted $C_{6-12}$aryl;
$R^2$ is one of hydrogen, $C_{1-8}$alkyl, $C_{3-8}$cycloalkyl or $C_{6-12}$aryl;
$R^3$ is one of hydrogen, hydroxy or $C_{1-8}$alkoxy;
$R^4$ is one of —$NH_2$, substituted phenyl, piperidinyl, quinuclidinyl or pyridyl, wherein said phenyl is substituted and said pyridyl is optionally substituted with one or two of halogen, hydroxy, $C_{1-8}$alkoxy, amino, mono($C_{1-4}$)alkylamino, di($C_{1-4}$)alkylamino, or amino($C_{1-4}$)alkyl;
X is —C(O)—; and
n is zero to eight.

3. The compound of claim 2, wherein $R^1$ is $C_{6-10}$aryl that is optionally amino substituted.

4. The compound of claim 2, wherein
$R^1$ is phenyl, aminophenyl or naphthyl;
$R^2$ is hydrogen or $C_{1-4}$alkyl;
$R^3$ is hydrogen, hydroxy, or $C_{1-4}$alkoxy; and
$R^4$ is one of —$NH_2$, [phenyl], pyridyl, 3-hydroxyphenyl, 4-hydroxyphenyl, 4-hydroxy-3-methoxyphenyl, 3-hydroxy-4-methoxyphenyl, 4-dimethylaminophenyl or 3-aminomethylphenyl.

5. The compound of claim 4, wherein $R^4$ is —$NH_2$, and n is from 1–8.

6. The compound of claim 5 wherein n is one of 3, 4 or 7.

7. The compound of claim 4 wherein $R^4$ is one of pyridyl, 3-hydroxyphenyl, 4-hydroxyphenyl, 4-hydroxy-3methoxyphenyl, 3-hydroxy -4-methoxyphenyl, 4-dimethylaminophenyl and 3-aminomethylphenyl, and n is one of zero or one.

8. The compound of claim 1 which is 3-[(2-naphthalenylsulfonyl)amino]-N-[2-hydroxy-2-(3'-hydroxyphenyl)ethyl]benzamide.

9. The compound of claim 1 which is 3-[(2-naphthalenylsulfonyl)amino]-N-[4'-[(N',N'-dimethylamino)phenyl]methyl]benzamide.

10. The compound of claim 1 which is 3-[(2-naphthalenylsulfonyl)amino]-N-[(2'-pyridyl)methyl]benzamide.

11. The compound of claim 1 which is 3-[(2-naphthalenylsulfonyl)amino]-N-(5-aminopentyl)benzamide.

12. The compound of claim 1 which is 3-[(phenylsulfonyl)amino]-N-[(4-hydroxy-3'-methoxyphenyl)methyl]benzamide.

13. The compound of claim 1 which is 3-[(phenylsulfonyl)amino]-N-[2-hydroxy-2-(4'-hydroxy-3'-methoxyphenyl)ethyl]benzamide.

14. The compound of claim 1 which is 3-[(3'-aminophenylsulfonyl)amino]-N-[4'-[(N',N'-dimethylamino)phenyl]methyl]benzamide.

15. A compound of claim 1, which is one of:

3-[(2-naphthalenylsulfonyl)amino]-N-[2-hydroxy-2-(3'-hydroxyphenyl)ethyl]benzamide;
3-[(2-naphthalenylsulfonyl)amino]-N-[2-hydroxy-2-(4'-hydroxyphenyl)ethyl]benzamide;
3-[(2-naphthalenylsulfonyl)amino]-N-[4'-[(N',N'-dimethylamino)phenyl]methyl]benzamide;
3-[(phenylsulfonyl)amino]-N-[(4-hydroxy-3-methoxyphenyl)methyl]benzamide;
3-[(phenylsulfonyl)amino]-N-[2-hydroxy-2-(3'-hydroxyphenyl)ethyl]benzamide;
3-[(phenylsulfonyl)amino]-N-[2-hydroxy-2-(4'-hydroxy-3'-methoxyphenyl)ethyl]benzamide;
3-[(phenylsulfonyl)amino]-N-[2-(3'-hydroxy-4-methoxyphenyl)ethyl]benzamide;
'3-[(phenylsulfonyl)amino]-N-[(3'-aminomethylphenyl)methyl]benzamide hydrochloride salt;
3-[(2-naphthalenylsulfonyl)amino]-N-[(2'-pyridyl)methyl]benzamide;
3-[(2-naphthalenylsulfonyl)amino]-N-[(3'-aminomethylphenyl)methyl]benzamide;

3-[(phenylsulfonyl)amino]-N-(4-aminobutyl)benzamide;

3-[(3'-aminophenylsulfonyl)amino]-N-[4'-[(N',N'-dimethylamino)phenyl]methyl]benzamide;

3-[(2-naphthalenylsulfonyl)amino]-N-(5-aminopentyl)benzamide; or

3-[(2-naphthalenylsulfonyl)amino]-N-(8-aminooctyl)benzamide.

16. A pharmaceutical composition comprising a compound of claim 1, and a pharmaceutically acceptable carrier or diluent.

17. A method of treating thrombosis, ischemia, stroke, restenosis or inflammation comprising administering to a mammal in need of said treatment a therapeutically or prophylactically effective amount of a compound having the Formula I:

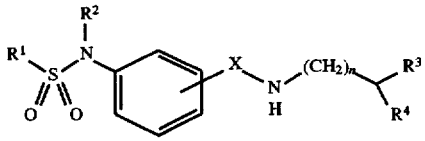

or a pharmaceutically acceptable salt thereof;
  wherein
    $R^1$ is alkyl, substituted alkyl, cycloalkyl, aryl, or substituted aryl;
    $R^2$ is one of hydrogen, alkyl, cycloalkyl, aryl or aralkyl;
    $R^3$ is one of hydrogen, hydroxy or alkoxy;
    $R^4$ is one of —$NH_2$, phenyl, or a $C_{3-10}$heterocycle selected from the group consisting of quinuclidinyl, piperidinyl, morpholinyl, pyrrolidinyl, pyridinyl, pyrimidinyl and imidazole, wherein said phenyl and said $C_{3-10}$heterocycle are optionally substituted with one or two of halogen, hydroxy, hydroxyalkyl, alkoxy, amino, monoalkylamino, dialkylamino, aminoalkyl, monoalkylaminoalkyl, and/or dialkylaminoalkyl;
    X is one of —$CH_2$— or —$C(O)$—;
    n is from zero to eleven; and
  wherein X is attached to the benzene ring in a position ortho-, meta- or para- to the sulfonylamino group;
  provided that when $R^4$ is —$NH_2$, then $R^3$ is hydrogen and n is other than zero; and also provided that when $R^3$ is hydroxy or alkoxy, then $R^4$ is other than —$NH_2$, and n is other than zero.

18. The method of claim 17, wherein said compound is one of:

3-[(2-naphthalenylsulfonyl)amino]-N-[2-hydroxy-2-(3'-hydroxyphenyl)ethyl]benzamide;

3-[(2-naphthalenylsulfonyl)amino]-N-[2-hydroxy-2-(4'-hydroxyphenyl)ethyl]benzamide;

3-[(2-naphthalenylsulfonyl)amino]-N-[4'-[(N',N'dimethylamino)phenyl]methyl]benzamide;

3-[(phenylsulfonyl)amino]-N-[(4-hydroxy-3-methoxyphenyl)methyl]benzamide;

3-[(phenylsulfonyl)amino]-N-[2-hydroxy-2-(3'-hydroxyphenyl)ethyl]benzamide;

3-[(phenyl sulfonyl)amino]-N-[2-hydroxy-2-(4'-hydroxy-3-methoxyphenyl)ethyl]benzamide;

3-[(phenylsulfonyl)amino]-N-[2-(3'-hydroxy-4'-methoxyphenyl)ethyl]benzamide;

3-[(phenylsulfonyl)amino]-N-[(3'-aminomethylphenyl)methyl]benzamide hydrochloride salt;

3-[(2-naphthalenylsulfonyl)amino]-N-[(2'-pyridyl)methyl]benzamide;

3-[(2-naphthalenylsulfonyl)amino]-N-[(3'-aminomethylphenyl)methyl]benzamide;

3-[(phenylsulfonyl)amino]-N-(4-aminobutyl)benzamide;

3-[(3'-aminophenylsulfonyl)amino]-N- [4'-[(N',N'-dimethylamino)phenyl]methyl]benzamide;

3-[(2-naphthalenylsulfonyl)amino]-N-(5-aminopentyl)benzamide; or

3-[(2-naphthalenylsulfonyl)amino]-N-(8-aminooctyl)benzamide.

19. The method of claim 17, wherein
  $R^1$ is optionally substituted $C_{6-12}$aryl;
  $R^2$ is one of hydrogen, $C_{1-8}$alkyl, $C_{3-8}$cycloalkyl or $C_{6-12}$aryl;
  $R^3$ is one of hydrogen, hydroxy or $C_{1-8}$alkoxy;
  $R^4$ is one of —$NH_2$, phenyl, piperidinyl, quinuclidinyl or pyridyl, wherein said phenyl and pyridyl are optionally substituted with one or two of halogen, hydroxy, $C_{6-8}$alkoxy, amino, mono($C_{1-4}$)alkylamino, di($C_{1-4}$)alkylamino, amino($C_{1-4}$)alkyl; and
  X is —$C(O)$—; and n is zero to eight.

20. The method of claim 19, wherein $R^1$ is $C_{6-10}$aryl that is optionally amino substituted.

21. The method of claim 19, wherein
  $R^1$ is phenyl, aminophenyl or naphthyl;
  $R^2$ is hydrogen or $C_{1-4}$alkyl;
  $R^3$ is hydrogen, hydroxy or $C_{1-4}$alkoxy; and
  $R^4$ is one of —$NH_2$, phenyl, pyridyl, 3-hydroxyphenyl, 4-hydroxyphenyl, 4-hydroxy-3-methoxyphenyl, 3-hydroxy-4-methoxyphenyl, 4-dimethylaminophenyl and 3-aminomethylphenyl.

22. The method of claim 21, wherein $R^4$ is —$NH_2$, and n is from 1–8.

23. The method of claim 22, wherein n is one of 3, 4 or 7.

24. The method of claim 21, wherein $R^4$ is one of pyridyl, 3-hydroxyphenyl, 4-hydroxyphenyl, 4-hydroxy-3-methoxyphenyl, 3-hydroxy-4-methoxyphenyl, 4-dimethylaminophenyl and 3-aminomethylphenyl, and n is one of zero or one.

25. A compound having the Formula I:

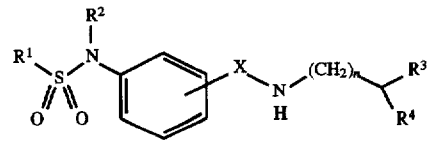

or a pharmaceutically acceptable salt thereof;
  wherein
    $R^1$ is heteroaryl or substituted heteroaryl;
    $R^2$ is one of hydrogen, alkyl, cycloalkyl, aryl or aralkyl;
    $R^3$ is one of hydrogen, hydroxy or alkoxy;
    $R^4$ is one of —$NH_2$, phenyl, or a $C_{3-10}$heterocycle selected from the group consisting of quinuclidinyl, piperidinyl, morpholinyl, pyrrolidinyl, pyridinyl, pyrimidinyl and imidazole, wherein said phenyl and said $C_{3-10}$heterocycle are optionally substituted with one or two of halogen, hydroxy, hydroxyalkyl, alkoxy, amino, monoalkylamino, dialkylamino, aminoalkyl, monoalkylaminoalkyl, and/or dialkylaminoalkyl;
    X is one of —$CH_2$— or —$C(O)$—;
    n is from zero to eleven; and
  wherein
    X is attached to the benzene ring in a position ortho-, meta- or para- to the sulfonylamino group;

provided that when $R^4$ is $-NH_2$, then is hydrogen and n is other than zero; further provided that when $R^3$ is hydroxy or alkoxy, then $R^4$ is other than $-NH_2$, and n is other than zero.

26. A compound of claim 25, wherein $R^1$ is pyridyl, thienyl, chromenyl, benzoxazolyl, quinazolinyl, quinolinyl or tetrahydroquinolinyl, any of which is optionally substituted by one or more of halogen, $C_{1-6}$alkyl, $C_{1-6}$alkoxy, carboxy, amino, $C_{1-6}$alkylamino or di($C_{1-6}$)alkylamino.

27. A pharmaceutical composition comprising a compound of claim 25, and a pharmaceutically acceptable carrier or diluent.

\* \* \* \* \*